United States Patent [19]

Grobbelaar et al.

[11] 4,280,625
[45] Jul. 28, 1981

[54] SHADE DETERMINATION

[76] Inventors: Jacobus H. Grobbelaar, 18 Truro St., Alberton, Transvaal; Richard N. Colson, 23 Harry van Wyk Ave., Kempton Park, Transvaal; Charlie M. Levitt, 40 Craighall Rd., Victory Park, Transvaal; Samuel Chatterley, 1 Riethaan St., Florida Lake, Transvaal, all of South Africa

[21] Appl. No.: 22,514

[22] Filed: Mar. 21, 1979

[30] Foreign Application Priority Data

Apr. 3, 1978 [ZA] South Africa .................. 78/1879
Apr. 3, 1978 [ZA] South Africa .................. 78/1880

[51] Int. Cl.³ .............................................. B07C 5/342
[52] U.S. Cl. .................................. 209/582; 209/585; 209/655; 250/222 R; 356/341; 356/342
[58] Field of Search ............... 209/582, 581, 580, 585, 209/655, 587; 356/338, 341, 342, 343; 250/205, 222 R, 233

[56] References Cited

U.S. PATENT DOCUMENTS

| 3,189,178 | 6/1965 | Calleson et al. ............... 209/655 X |
| 3,543,925 | 12/1970 | Loughery .................... 209/655 X |
| 3,750,882 | 8/1973 | Hays ........................ 209/580 |
| 3,782,544 | 1/1974 | Perkins ...................... 209/580 X |
| 3,886,354 | 5/1975 | Swidén ....................... 250/233 |

Primary Examiner—Allen N. Knowles
Attorney, Agent, or Firm—Haseltine and Lake

[57] ABSTRACT

The invention relates to the measurement of the shade of a particle. The particle is illuminated with light of variable intensity and viewed against a background level of illumination. A measurement is made of the ratio of time for which the intensity of light from the particle exceeds the intensity of the background to obtain a measurement of the shade of the particle.

15 Claims, 9 Drawing Figures

SHADE DETERMINATION

BACKGROUND OF THE INVENTION

This invention relates to the determination of shade.

Particles such as gemstones, particularly diamonds, can be sorted according to their colour and their shade. For example, between the colours white and black there is a variety of shades of grey, all of which have the same relative proportions of the primary colours. The difference between a white surface and a grey surface is that the former reflects most of the light which falls on its whereas the latter absorbs an appeciable fraction of the light, and reflects the rest.

In the diamond industry increasing use is being made of machinery for automatically sorting diamonds according to their colour. A colour determination of a diamond can be effected, for example, by determining the relative intensities of the primary colours reflected by the diamond. Such a determination is, however, independent of shade.

One way in which the shade of a particle is assessed is to compare the particle against differently shaded illuminated backgrounds. When a particle of a particular shade is viewed against a background of the same shade the particle apparently vanishes. If this viewing is done electronically, for example, by means of a photodetector which is responsive to the intensity of light on the background, it is found that there is no change in the detector output when the particle and the background are of the same shade. However, if the particle is not of the same shade as the background the output signal of the detector changes in amplitude. The change in amplitude of the detector signal is a function of the shade of the particle and of the size of the particle. In existing methods of shade sorting no attempt is made to record the actual amplitude of the signal produced. The sort is made simply on the basis of whether the output signal amplitude changes positively or negatively relative to a null value. Hence the fact that the amplitude of this signal is size dependent is not of any consequence.

The particles which cause a positive or a negative signal can be ejected at each pass, their shades being lighter or darker than the background in use. Hence one pass through the sorting machine and a different background is required to sort each shade.

SUMMARY OF THE INVENTION

It is an object of the present invention to provide an improved method of determining the shade of a particle.

The invention provides a method of determining the shade of a particle which includes the steps of providing a reference level of illumination, illuminating the particle, the relative intensities of the reference level of illumination and of the particle illumination varying, and comparing the intensity of light from at least the particle to the intensity of the reference level of illumination to obtain a measure of the shade of the particle.

Further according to the invention the reference level is provided by an illuminated background, the particle being illuminated while it is positioned in front of a given area of the background and the intensity of light from the particle and from the given area of the background is compared to the intensity of the illuminated background.

The method of the invention further includes the step of obtaining a measure of the period for which the intensity of light from the particle and from the given area of the background is greater than or is below the intensity of the illuminated background over a given time interval.

The ratio of the measured period to the given time interval may be determined to obtain a measure of the shade of the particle.

Further according to the invention the particle is illuminated while it is positioned in front of, and is falling freely towards, the background.

Further according to the invention the particle is illuminated substantially uniformly from all sides.

Although it falls within the scope of the invention to illuminate the particle with light which is of substantially constant intensity, and to have the reference level of illumination of variable intensity, it is preferred that the particle is illuminated with light of variable intensity, and the reference level of illumination is substantially constant.

The intensity of the light may oscillate and preferably is saw-tooth modulated.

The invention also provides apparatus for determining the shade of a particle which comprises means for providing a reference level of illumination, means for illuminating the particle, the relative intensities of the reference level of illumination and of the particle illumination varying, and means for comparing the intensity of light from at least the particle to the intensity of the reference level of illumination to obtain a measure of the shade of the particle.

Further according to the invention the means for providing the reference level of illumination comprises a background and a light source to illuminate the background, the particle being illuminated while it is located in front of a given area of the background, and the comparison means compares the intensity of light from the particle and from the given area of the background to the intensity of the illuminated background.

Further according to the invention the apparatus includes means to obtain a measure of the period for which the intensity of light from the particle and from the given area of the background is greater than or is below the intensity of the illuminated background, over a given time interval, and means for determining the ratio of the measured period to the given interval.

Further according to the invention the comparison means includes detector means which is responsive to the intensity of the illuminated background and the particle illuminating means includes a light source, an integrating sphere, an aperture being formed through the wall of the sphere to admit light from the source into the sphere, the sphere being located in front of the background and including an inlet and an outlet which permit the passage of the particle through the sphere and the transmission of light from the given area of the background to the detector means.

BRIEF DESCRIPTION OF THE DRAWINGS

The invention is further described by way of example with reference to the accompanying drawings in which.

DESCRIPTION OF A PREFERRED EMBODIMENT

Figure 1:
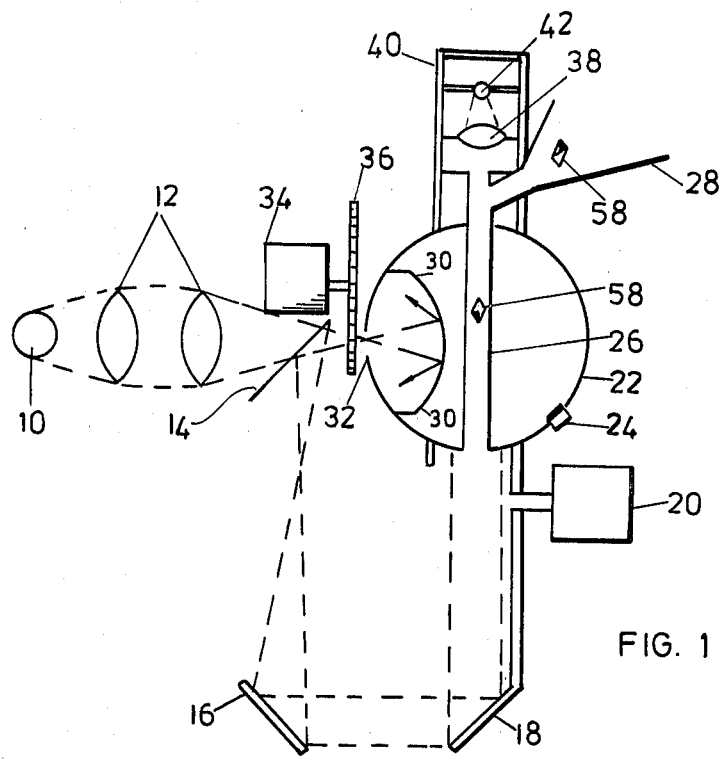
FIG. 1 is a schematic illustration of apparatus according to the invention.
Figure 2:
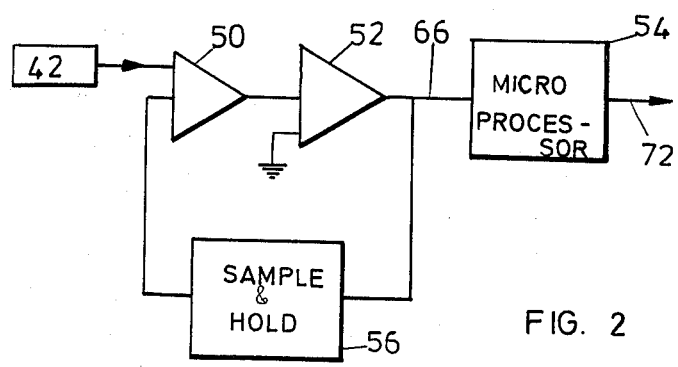
FIG. 2 is a block diagram of electrical apparatus used with the apparatus of FIG. 1.

Referring to FIGS. 1 and 2 the apparatus of the invention includes a lamp 10, a lens system 12, a beam splitter 14, a mirror 16, a background 18, an air ejector 20, an integrating sphere 22, a photodetector 24 mounted on the wall of the sphere, a glass tube 26 which extends through the sphere and which has an inlet funnel 28 formed at its upper end, a baffle 30 located inside the sphere opposite an aperture 32 formed in the wall of the sphere, a motor 34 and a toothed wheel 36 which is driven by the motor and which is located between the beam splitter 14 and the aperture 32, a lens 38 which is positioned inside a housing 40 above the upper end of the glass tube 26, and a photodetector 42 located above the lens 38.

The output signal of the photodetector 42 is connected to a differential amplifier 50, see FIG. 2, and this amplifier is connected to a zero crossing detector 52 whose output is connected to a micro processor 54 and to an automatic level controller and clamp 56.

Figure 3:
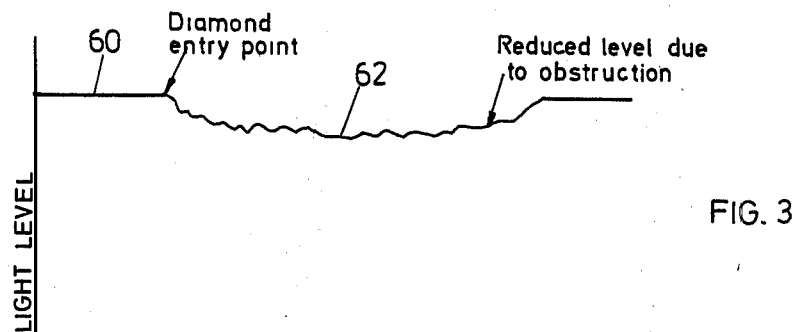

The apparatus of the invention functions as follows. Diamond particles 58 which are to be sorted according to their shades are introduced through the funnel 28 into the glass tube 26. The diamonds are admitted into the glass tube one at a time by means of suitable control devices, the arrangement being such that at any time only one particle is in the tube. Prior to the introduction of any particle into the glass tube the photodetector 42 is responsive to the light from the background 18 only. The background 18 is illuminated by light from the lamp 10 which passes through the lens system 12 and which is diverted by means of the beam splitter 14 onto the mirror 16 and then onto the background. Prior to the introduction of any particle into the glass tube, the toothed wheel is rotating at a constant speed causing a modulated light signal to pass through the aperture 32. However, due to the baffle 30 and the fact that the field of view of the detector 42 is restricted to the centre of the background 18 very little of this modulated light signal is allowed to reach the photodetector 42. During this phase the photodetector 42 is illuminated vertically only by the light from the background 18 and since this light intensity is constant the output signal of the photodetector 42 is also constant. This steady state condition is illustrated in the waveform of FIG. 3 by the line 60 of constant amplitude.

When a diamond particle 58 enters the glass tube 26, the toothed wheel 36 which is being rotated by the motor 34 allows light from the lamp 10 to pass through the aperture 32 into the sphere 22. The intensity of this light varies from darkness to maximum brightness and preferably the modulation of the light intensity with time is substantially saw-toothed. This is achieved inter alia by a correct choice of the motor speed, the size and number of the gaps in the toothed wheel 36 and the location of the focal point of the lens system 12.

The light passing through the aperture 32 is reflected by the baffle 30 onto the internal wall of the sphere 22. This wall is coated with a barium sulphate photometric paint of neutral spectral reflectance and the light incident on it is reflected in all directions inside the sphere with a minimum loss of amplitude and colour interference. The result is that a particle 58 inside the glass tube 26 is uniformly illuminated from all sides with light the intensity of which varies in saw-toothed fashion.

Light from the aperture 32 which via the internal wall of the sphere 22 is incident on the particle 58 as it tumbles down the glass tube 26 is reflected by the particle and some of it passes directly up the tube onto the photodetector 42.

If the aperture 32 were blocked and the particle 58 fell through the sphere its only effect would be to reduce the output signal of the photodetector 42. This is shown by the intermediate portion 62 of reduced amplitude of the waveform in FIG. 3. This reduced amplitude results because the particle prevents light from the background 18 reaching the photodetector. The larger the size of the particle the greater is the amount of light from the background 18 which is prevented from reaching the photodetector. As the particle falls through the tube its orientation constantly changes and subsequently the area and shade it presents to the background also changes. This accounts for the fluctuation in the amplitude of the output signal of the photodetector over the intermediate portion 62.

Figure 4:
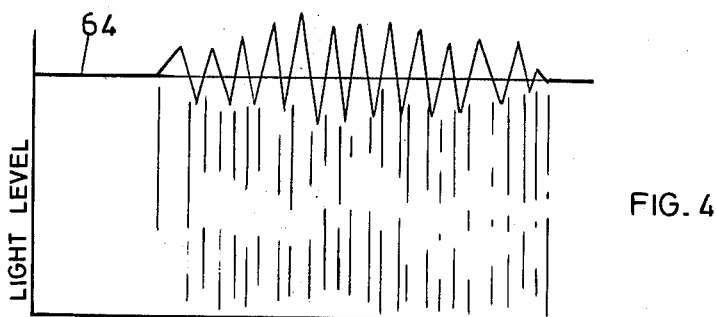

FIG. 4 illustrates the saw-tooth output signal of the photodetector 42 which results when the particle 58 is illuminated with light from the aperture 32 while it is falling through the glass tube 26. This output signal is the sum of two components, a first component which is the light from the background 18 which reaches the photodetector and which is equivalent to the output signal shown in FIG. 3, and a second component which is constituted by the light from the aperture 32 which is reflected by the particle 58 to the photodetector and which is simply superimposed on the output signal which arises from the background 18 only.

The amount of light which is reflected by the particle is dependent on the particle size and on the shade of the particle. However, referring to FIG. 4, at the instant when the saw-toothed amplitude of the output signal of the photodetector 42 is equal to the level 64 of the output signal which existed immediately before the particle was introduced into the glass tube 26 a condition is reached at which effectively the amount of light reflected by the particle is dependent on its shade only. At this instant if a particle were viewed against the background 18 it would apparently vanish. Since the particle during its passage through the sphere 22 is constantly being illuminated with light from the aperture 32 the output signal from the photodetector 42 is equal to the level 64 a number of times. A measure of the particle's shade can therefore be obtained by computing the ratio of the period for which the output signal of the photodetector is above the level 64 to the time which the particle takes to travel through the sphere.

Figure 5:
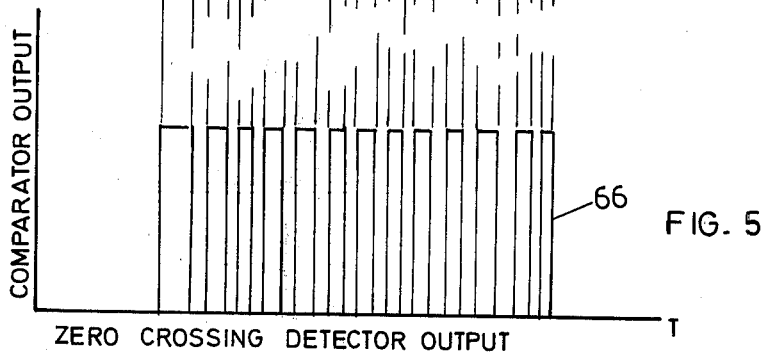

The circuitry of FIG. 2 carries out this calculation. The output signal of the photodetector 42 is connected to the differential amplifier 50 and after amplification is compared in the comparator 52 to a signal of zero amplitude. The comparator therefore functions as a zero crossing detector which generates a fixed amplitude pulse for the period for which the output signal of the photodetector is above the level 64. The output signal of the zero crossing detector is therefore a train 66, see FIG. 5, of fixed amplitude, variable duration pulses. The micro processor 54 is used to compute the average value of the zero crossing detector output. The average value which is computed by the microprocessor is used to drive a selectr unit illustrated in FIGS. 6 to 8 which routes the particle to a sort bin according to its shade.

The automatic level controller and clamp 56 is used to sample the light level 60 (or 64) which exists at the photodetector 42 immediately before the particle 58 enters the glass tube. This light level is held by the clamp for the period that the particles takes to pass through the sphere so that the zero crossing detector functions against a reference signal of fixed amplitude.

When the particle exits the sphere the air ejector 20 is used to divert the trajectory of the particle between the mirror 16 and the background 18. This prevents the background from being damaged by the impact of the particle. Once the particle has passed between the mirror and the background it is diverted by the selector unit to the correct sort bin. Alternatively, the exit of the particle from the sphere could be detected and the background 18 which can be mounted on a hinge, can be swung out of the path of movement of the particle which then passes directly to the selector unit. The signal produced by detecting the exit of the particle from the sphere can also be used to trigger the clamp 56 so that it samples and holds the output signal 64 of the photodetector which is dependent only on the intensity of the background level of illumination. The same signal can be used to trigger the control device which regulates the passage of the particles through the funnel 28 into the sphere.

The photodetector 24 samples the rate of change of the light intensity inside the sphere 22 and via a suitable feedback circuit controls the chopper motor 34 so that it rotates at a constant speed.

Figure 2A:
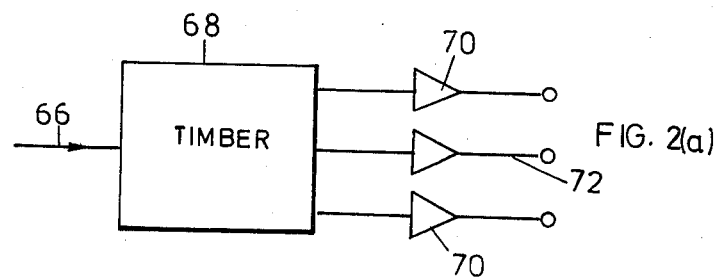
FIG. 2(a) illustrates a modification of the apparatus of FIG. 2, FIGS. 3, 4 and 5 are various waveforms which are generated in the apparatus of the invention.

The microprocessor 54 is used with a suitable analogue to digital converter interface in a preferred form of the invention to calculate the average value of the zero crossing detector output. The programme necessary for the calculation may, it is believed, easily be written by one skilled in the art. However, as an alternative use could be made of hardware to effect the necessary computations. For example, as shown in FIG. 2(a) the total period for which the pulse train 66 is above zero, over a fixed interval which is less than the time taken for a particle to traverse the sphere, could be accumulated by means of a simple timer 68. The accumulated times of different particles of varying standard shades could be recorded and a decision on the shade of a particle under test could be made by comparing the accumulated time for the particle under test to the reference times. This comparison could be effected with the aid of window comparators 70.

Figure 6:
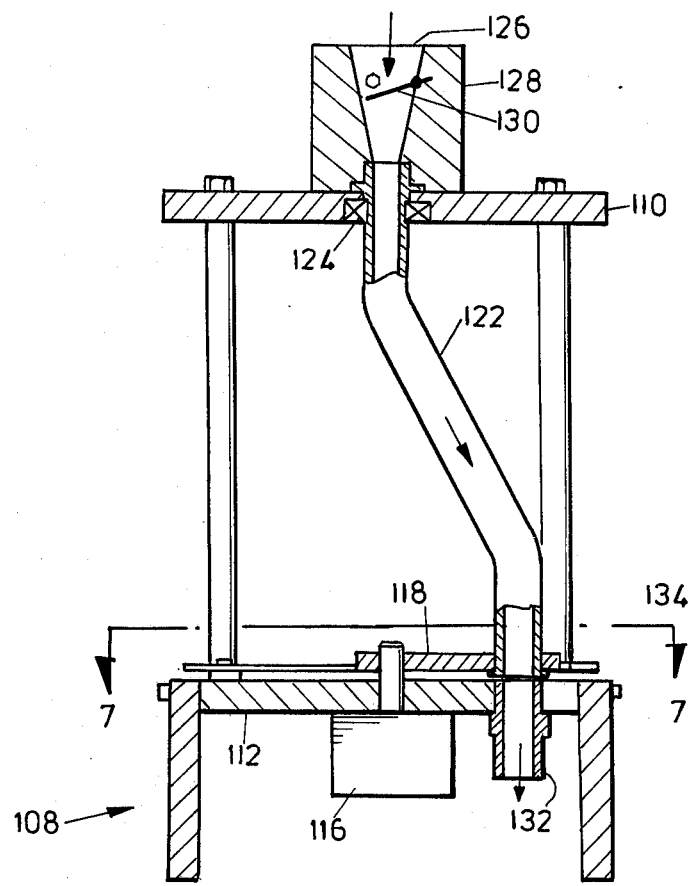
FIG. 6 is a side view, partly sectioned, of apparatus used in the invention.
Figure 7:
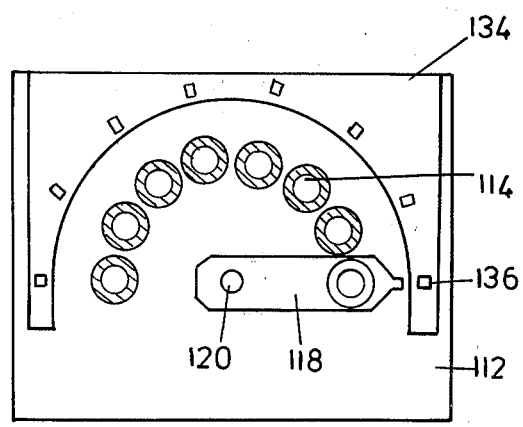
FIG. 7 is a section through the apparatus of FIG. 6 taken on the line 7—7.
Figure 8:
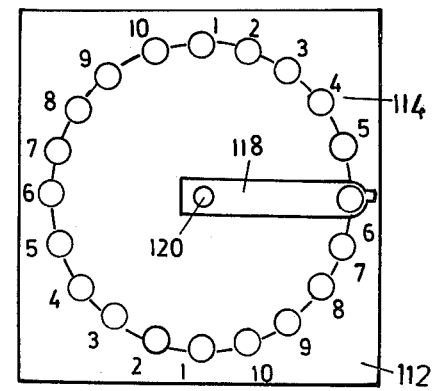
FIG. 8 is a section, similar to FIG. 7, of a modified sorting apparatus.

The output signals 72 of the comparators 70, or of the microprocessor 54, are used to control the selector apparatus shown in FIGS. 6 to 8. The selector apparatus 108 includes a supporting frame 110, a base plate 112 in which is formed a plurality of apertures 114 located on the arc of a circle, a stepping motor 116 attached to the underside of the base plate 112, an arm 118 which is fixed to a shaft 120 of the motor 116, and a guide tube 122.

The tube 122 is rotatably supported at its upper end by means of a bearing 124 secured to the supporting frame 110, and its lower end which is off set with respect to the upper end is attached to the arm 118. The bore of the tube 122 equals that of the apertures 114.

The upper end of the tube 122 mates with a funnel 126 which is formed in a housing 128. A gate 130 inside the funnel is used to control the passage of particles into the tube 122.

Each aperture 114 is connected to a tubular guide 132 which leads to a storage bin, not shown. The apertures are surrounded by a board 134 which carries a plurality of sensors 136, each sensor being associated with one of the apertures. Each sensor may, for example, consist of a light source and means to detect light reflected from the outer end of the arm.

The inlet of the funnel 126 is located below the sphere 22 so that particles falling from the sphere are captured by the funnel. When a particle enters the funnel it is trapped by the gate 130 until such time as the computations regarding its characteristics are completed and also to ensure that no particles are inside the guide tube. Once the particle held by the gate 130 has been categorised by the circuitry of FIG. 2 the guide tube 122 is moved into register with a selected aperture 114 by means of the stepping motor 116. The gate 130 is released allowing the particles to tumble through the guide tube, the aperture, and the tubular guide 132 into its storage bin. Alternatively, the arrangements could be such that the gate 130 is opened and the tube 122 is moved to its selected position while the particle is falling through it.

The signal 72 which is produced by the circuit of FIG. 2 is indicative of the shade of the diamond particle and is used to select the position to which the stepping motor 116 must be moved.

The position at any time of the stepping motor is sensed by the sensors 136. To ensure an optimum throughput of the selector apparatus the stepping motor can be microprocessor controlled to ensure that it is accelerated and decelerated at maximum rates while the tube 122 is moved between the various apertures 114.

If the stepping motor is of a high quality and is capable of being moved to a selected position with consistent accuracy the sensors 136 of the various apertures can be dispensed with. However, it may then be necessary to provide sensors at two positions simply to provide a check on the operation of the stepping motor.

The selection process provided by the apparatus of FIGS. 6 and 7 can be speeded up by adopting the construction illustrated in FIG. 8. In this case the apertures 114 are formed in two equal groups, with say ten apertures in each group. Each group is located on the circle along which the free end of the tube 122 rotates, and extends through 180°. In FIG. 8 the apertures in each group are numbered from 1 to 10. Each aperture in a group is located diametrically opposite the aperture with the same number in the other group. Thus the apertures numbered 2 oppose each other, and so on.

The like-numbered apertures are linked to each other on the underside of the base plate 112, and so discharge into the same storage bin.

The modified selector apparatus is used in the same way as the apparatus of FIGS. 6 and 7. However, the sorting rate is now considerably increased for the stepping motor need rotate only through a maximum angle of 90° to align the tube with an aperture associated with a particular sort category, i.e. storage bin.

The modification can be repeated to increase the number of apertures associated with each sort category or storage bin and so reduce the maximum angular movement demanded of the stepping motor to select any of the sort categories. Clearly, though, there are practical limits to this.

We claim:

1. Apparatus for determining the shade of a particle which comprises:
    (a) means for providing a reference level of illumination;
    (b) means for illuminating the particle, in which the relative intensities of the reference level of illumination and of the particle illumination varying; and
    (c) means for comparing the intensity of light from at least the particle to the intensity of the reference level to obtain a measure of the shade of the particle, said comparison means includes detector means which is being responsive to the intensity of the illuminated background and in which the particle illuminating means comprises a light source and an integrating sphere, an aperture being formed through a wall of the sphere to admit light from the source into the sphere, the sphere being located in front of the background and including an inlet and an outlet which permit the passage of the particle through the sphere and the transmission of light from the given area of the background to the detector means.

2. Apparatus according to claim 1 which includes means to vary the intensity of the light passing through the aperture into the sphere.

3. A method of determining the shade of a particle which comprises the steps of:
    providing a reference level of illumination by illuminating a background;
    illuminating the particle while it is positioned in front of a given area of the background, the relative intensities of the background reference level of illumination and of the particle illumination varying; and
    obtaining a measure of the intensity of the light from the particle and from the given area of background and a measure of the time period for which one intensity measurement is greater than the other intensity measurement over a given time interval to obtain a measure of the shade of the particle.

4. A method as recited in claim 3 which comprises the steps of: determining the ratio of the measured time period to the given time interval.

5. A method according to claim 3 in which the given time interval is the time for which the particle is positioned in front of the background.

6. A method according to claim 3 in which the particle is positioned in front of the background while it is in free fall.

7. A method according to claim 6 in which the particle is illuminated while it is falling towards the background.

8. A method according to claim 3 in which the particle is illuminated substantially uniformly from all sides.

9. A method according to claim 3 in which the particle is illuminated with light of variable intensity, and the reference level of illumination is substantially constant.

10. A method according to claim 9 in which the intensity of the light oscillates.

11. A method according to claim 10 in which the intensity of the light is saw-tooth modulated at a constant frequency.

12. Apparatus for determining the shade of a particle which comprises:
    a background;
    a light source for illuminating the background;
    means for illuminating the particle while it is positioned in front of a given area of background;
    means to vary the relative intensities of the background reference level of illumination and of the particle illumination;
    means for obtaining a measure of the intensity of light from the particle and from a given area of background, a measure of the intensity of the illuminated background and a measure of the time period for which one intensity measurement is greater than the other intensity measurement over a given time interval, to obtain a measure of the shade of the particle.

13. Apparatus as recited in claim 12 which comprises means for determining the ratio of the measured time period to the given time interval.

14. Apparatus according to claim 13 which includes means for sorting the particle according to the determined ratio, the sorting means comprising means to guide the particle and means responsive to the measured ratio for moving the guide means between a plurality of locations.

15. Apparatus according to claim 14 wherein the sorting means includes a surface in which a plurality of apertures located on an arc are formed, the guide means comprising a conduit which is rotatable about an axis which is concentric with a first end of the conduit, the particle being guided for movement into the conduit at the first end and the other end of the conduit being movable successively into register with the apertures thereby allowing the particle inside the conduit to pass through one of the apertures.

* * * * *